United States Patent
Hossainy et al.

(10) Patent No.: US 8,034,361 B2
(45) Date of Patent: *Oct. 11, 2011

(54) STENT COATINGS INCORPORATING NANOPARTICLES

(75) Inventors: Syed F. A. Hossainy, Fremont, CA (US); Murthy V. Simhambhatla, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 11/644,771

(22) Filed: Dec. 21, 2006

(65) Prior Publication Data

US 2007/0110787 A1    May 17, 2007

Related U.S. Application Data

(63) Continuation of application No. 10/293,175, filed on Nov. 12, 2002, now abandoned.

(51) Int. Cl.
*A61F 13/00* (2006.01)
*A61F 2/00* (2006.01)

(52) U.S. Cl. .................... 424/422; 424/423

(58) Field of Classification Search ............... None
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 4,977,901 A | 12/1990 | Ofstead | |
| 5,112,457 A | 5/1992 | Marchant | |
| 5,328,471 A | 7/1994 | Slepian | |
| 5,455,040 A | 10/1995 | Marchant | |
| 5,464,650 A | 11/1995 | Berg et al. | |
| 5,578,073 A | 11/1996 | Haimovich et al. | |
| 5,605,696 A | 2/1997 | Eury et al. | |
| 5,665,382 A | 9/1997 | Grinstaff et al. | |
| 5,667,767 A | 9/1997 | Greff et al. | |
| 5,670,558 A | 9/1997 | Onishi et al. | |
| 5,684,059 A * | 11/1997 | Salamone ................ | 523/107 |
| 5,700,286 A | 12/1997 | Tartaglia et al. | |
| 5,716,981 A | 2/1998 | Hunter et al. | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,871,437 A * | 2/1999 | Alt | |
| 5,873,904 A | 2/1999 | Ragheb et al. | |
| 5,971,954 A | 10/1999 | Conway et al. | |
| 5,980,928 A | 11/1999 | Terry | |
| 5,980,972 A | 11/1999 | Ding | |
| 5,981,568 A * | 11/1999 | Kunz et al. .................. | 514/411 |
| 6,015,541 A | 1/2000 | Greff et al. | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,143,037 A | 11/2000 | Goldstein et al. | |
| 6,153,252 A | 11/2000 | Hossainy et al. | |
| 6,165,212 A | 12/2000 | Dereume et al. | |
| 6,309,569 B1 * | 10/2001 | Farrar et al. ................ | 264/4.1 |
| 6,358,556 B1 * | 3/2002 | Ding et al. ................ | 427/2.24 |
| 6,656,506 B1 | 12/2003 | Wu et al. | |
| 6,719,998 B1 * | 4/2004 | Golomb et al. | |
| 6,730,313 B2 * | 5/2004 | Helmus et al. | |
| 7,008,642 B1 * | 3/2006 | Roorda et al. ................ | 424/489 |
| 7,070,809 B2 * | 7/2006 | Goupil et al. ................ | 424/489 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

OTHER PUBLICATIONS

U.S. Appl. No. 10/663,181, filed Sep. 15, 2003, Wu et al.
U.S. Appl. No. 10/663,568, filed Sep. 15, 2003, Wu et al.

* cited by examiner

*Primary Examiner* — Susan Tran

(74) *Attorney, Agent, or Firm* — Squire, Sanders & Dempsey (US) LLP

(57) ABSTRACT

Coatings for implantable medical devices including nanoparticles incorporating an active agent, and methods for fabricating the coatings.

15 Claims, 1 Drawing Sheet

US 8,034,361 B2

STENT COATINGS INCORPORATING NANOPARTICLES

CROSS REFERENCE

This application is a continuation of U.S. patent application Ser. No. 10/293,175, filed on Nov. 12, 2002 now abandoned, and hereby incorporates by reference the complete contents of this application in its entirety.

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

The ability to isolate the drug from contact with the solvents used in the coating process, or to minimize such contact, is desirable for preserving the therapeutic effect of the drug. It is also desirable to facilitate incorporation of hydrophilic drugs in stent coatings. Such incorporation can be sometimes difficult due to the hydrophobic nature of many stent coatings. The embodiments of the present invention address these and other needs by providing methods of incorporating drugs on stents or other implantable medical devices.

SUMMARY

According to one embodiment of the present invention, a method for incorporating an active agent on an implantable medical device, the method comprises fabricating nanoparticles containing the active agent, dispersing the nanoparticles in an organic phase to make a suspension, and applying the suspension onto the device. The nanoparticles can be fabricated by preparing a water-in-oil emulsion, comprising the therapeutically active agent dispersed in an organic solvent polymer solution, converting the water-in-oil emulsion to a water-in-oil-in-water emulsion, and extracting the organic solvent from the water-in-oil-in-water emulsion. The nanoparticles can also be fabricated by preparing a water-in-oil emulsion comprising a polymer and the therapeutically active agent, and extracting the organic solvent from the water-in-oil-in-water emulsion. The nanoparticles can also be fabricated by preparing a solution comprising the therapeutically active agent and a polymer in an organic solvent, and spraying the solution to form the nanoparticles. The nanoparticles can also be fabricated by preparing a solution comprising the therapeutically active agent and a polymer in an organic solvent, atomizing the solution by spraying, freezing the atomized solution, and extracting the organic solvent to form the nanoparticles. The nanoparticles can also be fabricated by preparing a water-in-oil emulsion comprising a cross-linkable compound, the therapeutically active agent and a cross-linking compound, and cross-linking the cross-linkable compound to form the nanoparticles.

According to another embodiment of the present invention, a coating for an implantable medical device comprising nanoparticles containing an active agent is provided, where the nanoparticles are incorporated into a polymer binder. The nanoparticles can be made of a polymer such as poly(L-glycolic acid), poly(D-lactic acid), poly(L-lactic acid), poly (L-lactide), poly(D,L-lactide), poly(glycolide), poly(butylene terephtalate-co-ethylene glycol), poly(ethylene-co-vinyl alcohol), poly(vinyl acetate), poly(butyl methacrylate), poly (methyl methacrylate), polyurethanes, poly(caprolactone), polyanhydrides, polydiaxanone, polyorthoesters, polyamino acids, poly(trimethylene carbonate), cellulose acetate phthalate, and mixtures and combinations thereof.

DETAILED DESCRIPTION

Figure 1A:
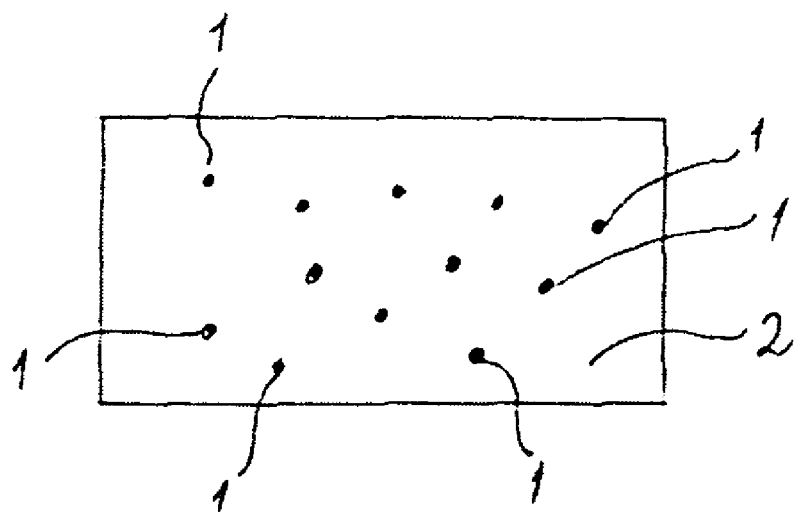
FIG. 1A shows schematically an emulsion made as a part of the process of fabricating nanoparticles.

A coating for an implantable medical device, such as a stent, according to one embodiment of the present invention, can include an optional primer layer, a drug-polymer layer or a drug layer free from any polymers, and an optional topcoat layer. The drug-polymer layer or the drug layer can be applied directly onto the stent surface. Alternatively, the drug-polymer layer can be applied onto the optional primer layer that can be used to improve adhesion of the coating to the stent. The optional topcoat layer can be applied onto the drug-polymer layer to allow better control of the rate of release of the drug from the device.

One way of incorporating a drug into the drug-polymer layer is by using particles of micron to sub-micron size. For the purposes of the present invention such particles having the drug incorporated therein are defined as "nanoparticles." The nanoparticles can be formed in a separate procedure, followed by suspending the nanoparticles in organic phase such as an organic solvent, for example methanol, or a solution of a polymer such as poly(ethylene-co-vinyl alcohol) (EVAL). The suspension can be then applied onto the stent to form the drug layer or the drug-polymer layer, respectively. The mass ratio between the nanoparticles and the polymer in the suspension can be within a range of between about 1:2 and 1:10.

The spherical or quasi-spherical particles can be made of a polymer encapsulating a drug. Typically, nanoparticles having the characteristic length (e.g., the diameter) between about 0.2 and 5.0 μm can be utilized. When the stent is in contact with body fluids, the polymer can swell and/or hydrolyze, thus releasing the drug. The particles can be made according to one of the methods described below.

1. The Double Emulsion Method

One method of fabricating the nanoparticles according to an embodiment of the present invention is the double emulsion technique. This procedure can be used when it is desirable to encapsulate water soluble drugs, peptides or proteins. For the purposes of the present invention, the term "water soluble" is defined as small molecule drugs, peptides, oligonucleotides, plasmids, or proteins that can form aqueous solutions having concentrations within a range between about 3 and 20 mass %. Examples of typical drugs that can be used include heparin, hyaluronic acid, L-arginine, D-arginine, polymers and/or oligomers of L-arginine, or D-arginine, gene encoding vascular endothelial growth factor (VEGF) and its isoforms and gene encoding nitric oxide synthase (NOS) and its isoforms.

An example of a peptide suitable for incorporation in the nanoparticles is poly(L-arginine). Alternatively, poly(D-arginine), poly(D,L-arginine), poly(L-lysine), poly(D-lysine), and poly(δ-guanidino-α-aminobutyric acid) can be used. Those having ordinary skill in the art may choose to use other appropriate drugs, peptides or proteins, if desired.

As a first step, a solution of an encapsulating polymer in a suitable organic solvent can be prepared (solution I). The concentration of the encapsulating polymer in solution I can be between about 2.0% w/v and about 20% w/v. One example of a suitable encapsulating polymer is poly(L-glycolic acid) (PLGA). Alternatively, poly(D-lactic acid) (PDLA), poly(L-lactic acid) (PLLA), poly(L-lactide), poly(D,L-lactide), poly(glycolide), poly(butylene terephtalate-co-ethylene glycol) (PBT-PEG), poly(ethylene-co-vinyl alcohol) (EVAL®), other vinyl polymers such as poly(vinyl acetate) (PVA), acrylic polymers such as poly(butyl methacrylate) (PBMA) or poly(methyl methacrylate) (PMMA), polyurethanes, poly(caprolactone), polyanhydrides, polydiaxonone, polyorthoesters, polyamino acids, poly(trimethylene carbonate), and mixtures and combinations thereof. Examples of organic solvents that can be used include methylene chloride, cyclooctane, cyclohexane, cycloheptane, para-xylene, dimethylformamide, dimethylsulfoxide, chloroform, dimethylacetamide, or mixtures thereof. Those having ordinary skill in the art will select other encapsulating polymers and solvents, if desired.

As a second step, an aqueous solution of a drug can be prepared (solution II) by dissolving the drug in de-ionized water. The solution can be plain or buffered. Optionally, viscosity enhancing agents and/or drug stabilizing agents such as poly(vinylpyrrolidone) or carboxymethylcellulose can be added to the solution II in the amount of about 0.01% w/v to about 0.5% w/v. Excipients (inert substances used as diluents or vehicles for a drug) and drug stabilizing agents may optionally be added to solution II.

As a third step, the organic phase (solution I) can be combined with the aqueous phase (solution II) and the blend of the two solutions is treated by ultrasound (sonicated) according to techniques known to those having ordinary skill in the art to yield a microfine water-in-oil (W-O) emulsion. Standard sonication equipment can be used. Alternatively, solution I can be vigorously stirred or vortexed while solution II is slowly added to solution I also resulting in the W-O emulsion. The emulsion is comprised of the aqueous phase 1 dispersed in the organic phase 2 (FIG. 1A).

As a fourth step, an aqueous solution of an emulsifier can be prepared (solution III) by dissolving the emulsifier in de-ionized water. The concentration of the emulsifier (surfactant) can be within a range of between 0.01% w/v and 0.5% w/v. One example of a suitable emulsifier is poly(vinyl alcohol) (PVA). Examples of the alternative emulsifiers that can be used include albumin (either bovine or human serum), gelatin, lipophilic emulsifiers such as PLURONIC® or TETRONIC®, or a combination thereof can be optionally added to stabilize the primary emulsion. PLURONIC® is a trade name of poly(ethylene oxide-co-propylene oxide). TETRONOC® is a trade name of a family of non-ionic tetrafunctional block-copolymer surfactants. PLURONIC® and TETRONIC® are available from BASF Corp. of Parsippany, N.J.

Figure 1B:
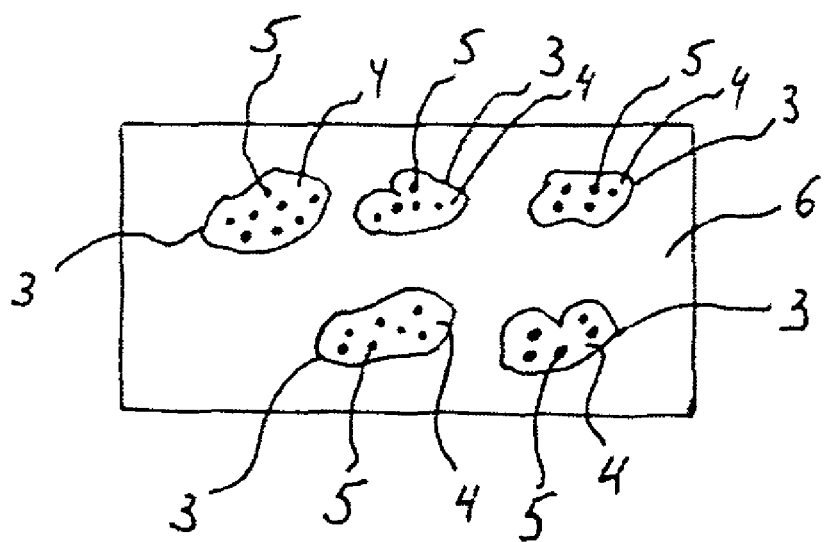
FIG. 1B shows schematically a double emulsion which includes nanoparticles.

Solution III can be vigorously stirred while the W-O emulsion is slowly added to solution III to produce a double emulsion also referred to as water-oil-water (W-O-W) emulsion. The double emulsion is comprised of nanoparticles 3 dispersed in the aqueous phase 6 (FIG. 1B). The nanoparticles are comprised of the encapsulating polymer 4 and the drug 5 contained within the encapsulating polymer.

As the fifth step, the double emulsion can then be stirred in excess of water to extract the organic solvent present in the organic phase 2 inside the nanoparticles 3. Instead of water, an aqueous solution of a water-soluble organic substance such as iso-propanol can be used. Alternatively, the organic solvent can be removed from the organic phase 2 by evaporation, optionally under suitable vacuum. The hardened nanoparticles can then be collected by filtration, sieving or centrifugation and lyophilized to form a free-flowing dry powder of nanoparticles.

2. The Water-in-Oil Emulsion Method

Another method of fabricating the nanoparticles according to an embodiment of the present invention includes preparing a water-in-oil emulsion followed by evaporation of solvent.

As a first step, a solution containing about 10 mass % of an encapsulating polymer in an organic solvent can be prepared. One example of the encapsulating polymer that can be used according to this technique is cellulose acetate phthalate (CAP) available from FMC Biopolymers Co. of Philadelphia, Pennsylvania under the trade name AQUACOAT®. Those having ordinary skill in the art will select other suitable encapsulating polymers, if desired. A drug, for example, everolimus, trapidil, or cisplatin is dispersed in the CAP solution, to make a drug-polymer dispersion which can contain about 5 mass % of the drug. Everolimus is the name of 40-O-(2-hydroxy)ethyl-rapamycin available from Novartis.

As a second step, liquid paraffin can be combined with a suitable surfactant, and the blend can be vigorously stirred. The paraffin-surfactant composition can contain about 1 mass % of the surfactant. Sorbitan oleate is one example of a suitable surfactant, but those having ordinary skill in the art will select other appropriate surfactants if necessary. Sorbitan oleate is available form ICI Americas, Inc. of Bridgewater, N.J. under a trade name SPAN 80.

As a third step, the drug-polymer solution can be added to the paraffin-based composition and the solvent is allowed to evaporate for about 24 hours at a temperature of about 30° C. As a result, the nanoparticles are formed, collected, washed with ether and dried at room temperature for about 24 hours.

3. The Spray-Drying Method

Yet another method of fabricating the nanoparticles according to an embodiment of the present invention is the spray drying technique. This procedure can be used when it is desirable to encapsulate drugs soluble in organic solvents. According to this technique, the solution comprising a drug and an encapsulating polymer can be dissolved in an appropriate organic solvent in which both the drug and the encapsulating polymer are soluble. One example of a suitable solvent can be methylene chloride. The solution can then be spray dried according to a method known to those having ordinary skill in the art. As a result, nanoparticles are formed comprising the drug encapsulated in the polymer.

One variation of the spray-drying methods can be used with drugs which are water-soluble but not soluble in common organic solvents. Such drugs can be first formulated as lyophilized powder. The drug powder can be suspended in a polymer phase comprising a suitable encapsulating polymer dissolved in a volatile organic solvent such as methylene chloride. The suspension can then be spray dried to produce the nanoparticles containing the drug.

4. The Cryogenic Method

Another method of fabricating the nanoparticles according to an embodiment of the present invention is the cryogenic technique. This procedure can be used for processing sensitive drugs such as proteins. The drug formulated as a lyophilized powder can be suspended in a polymer phase comprising a suitable encapsulating polymer dissolved in a volatile organic solvent such as methylene chloride. The suspension can be atomized by spraying into a container containing frozen ethanol overlaid with liquid nitrogen. The system can then be warmed to about −80° C. to liquefy the ethanol and extract the organic solvent from the microspheres. The hardened microspheres are collected by filtration or centrifugation and lyophilized.

5. The Cross-Linking Method

Another method of fabricating the nanoparticles according to an embodiment of the present invention is the cross-linking method. This procedure can be used if the selected encapsulating polymer is a thermoset polymer, and therefore can be cured by cross-linking. The cross-linking method uses at least two unsaturated compounds, one of which serving as a cross-linking agent.

A solution of a water-soluble unsaturated monomer, for example, vinyl pyrrolidone (VP) in water can be prepared. The concentration of VP in the solution can be between about 5.0 and 20.0 mass %. Alternative monomers, for example, hydroxyethyl methacrylate can be used in addition to, or instead of, VP. A water-soluble cross-linking agent can then be added to the solution of VP, for example, poly(ethylene glycol diacrylate) (PEG-DA) having a weight average molecular weight of about 1,000, to form the aqueous VP/PEG-DA solution (solution IV). The concentration of PEG-DA in solution IV can be between about 5.0 and 20.0 mass %. Alternative cross-linking agents such as other diacrylates or dimethacrylates can be selected by those having ordinary skill in the art to be used in addition to, or instead of PEG-DA. A hydrophobic drug, for example, enerolimus can be added to solution IV in the amount of between about 5.0 and 20.0 mass % of solution IV, forming a suspension of the drug in solution IV ("the drug suspension").

A separate solution of a photoinitiator such as 2,2-dimethoxy-2-phenyl acetophenone in VP can be made, the solution containing between about 5.0 and 20.0 mass % of the photoinitiator. Other photoinitiators, for example, dithiocarbonates or periodide can be used in the alternative. The photoinitiator solution is added to the drug suspension to form the final blend. The ratio between the photoinitiator solution and the drug suspension can be determined by those having ordinary skill in the art.

The final blend can be added into a viscous mineral oil or silicone oil and vortexed energetically until a W-O emulsion is formed. The emulsion can then be irradiated at 360 nm wavelength using a black ray UV-lamp for about 15 to 45 seconds. As a result, VP and PEG-DA copolymerize and VP is cross-linked with PEG-DA forming VP/PEG-DA nanoparticles containing the drug. The particles can then be isolated by decanting the oil phase, washed in acetone and dried.

If desired, an inorganic cross-linking agent can be used. For example, an encapsulating polymer/drug suspension can be made by mixing an aqueous solution containing about 10 mass % of poly(alginate) and enerolimus. The amount of the drug can be about 5 mass % of the poly(alginate) solution. The polymer/drug suspension is then combined with a solution of the cross-linking agent such as calcium chloride ($CaCl_2$) in de-ionized water. The amount of $CaCl_2$ can be about 10 mass % of the polymer/drug suspension. The polymer/drug/$CaCl_2$ system can be vigorously stirred leading to cross-linking of poly(alginate) forming the cross-linked poly (alginate) nanoparticles containing the drug. The particles are then isolated by decanting, washed in de-ionized water and dried.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN® available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. TAXOTERE®, from Aventis S. A., Frankfurt, Germany) methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (bivalirudin, Biogen, Inc., Cambridge, Mass.). Examples of such cytostatic or antiproliferative agents include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the name of everolimus, available from Novartis), 40-O-(3-hydroxy)propyl-rapamycin, 40-O-[2-(2-hydroxy)ethoxy]ethyl-rapamycin, and 40-O-tetrazole-rapamycin.

The coatings and methods of the present invention have been described in conjunction with a stent. The stent can be balloon-expandable or self-expandable. There are no limitations on the size of the stent, its length, diameter, strut thickness or pattern. The use of the coating is not limited to stents and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE® and ENDOTAK®, available from Guidant Corporation). The underlying structure of the device can be of virtually any design. The device can be made of a metallic material or an alloy such as, but not limited to, cobalt-chromium alloys (e.g., ELGILOY®), stainless steel (316 L), "MP35N," "MP20N," ELASTINITE® (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

Some embodiments of the present invention are illustrated by the following Examples.

Example 1

A polymer solution containing between about 0.1 mass % and about 15 mass %, for example, about 2.0 mass % of EVAL and the balance, dimethyl acetamide (DMAC) solvent, can be prepared. The solution can be applied onto a stent to form a primer layer. To apply the primer layer, a spray apparatus, such as an EFD 780S™ spray nozzle with a VALVEMATE™ 7040 control system, manufactured by EFD, Inc. of East Providence, R.I. can be used. The EFD 780S spray nozzle is an air-assisted external mixing atomizer. The composition can be atomized by air and applied to the stent surfaces. During the process of applying the composition, the stent can be optionally rotated about its longitudinal axis, at a speed of 50 to about 150 rpm. The stent can also be linearly moved along the same axis during the application.

The EVAL solution can be applied to a 13-mm TETRA® stent (available from Guidant Corporation) in a series of 10-second passes, to deposit, for example, 10 μg of coating per spray pass. Instead of the 13-mm TETRA stent, another suitable stent can be used, for example, a 12-mm VISION® stent (also available from Guidant Corporation). Between the spray passes, the stent can be dried for about 10 seconds using flowing air with a temperature of about 60° C. Five spray passes can be applied, followed by baking the primer layer at about 140° C. for one hour. As a result, a primer layer can be formed having a solids content of about 50 μg. "Solids" means the amount of the dry residue deposited on the stent after all volatile organic compounds (e.g., the solvent) have been removed.

Next, a polymer solution containing between about 10 mass % and about 25 mass %, for example, about 18 mass % of EVAL and the balance, dimethyl sulfoxide (DMSO) solvent, can be prepared, by mixing EVAL and DMSO and heating the mixture to about 50° C. while constantly stirring. Another solvent, dimethyl formamide (DMF) can be added to the EVAL/DMSO solution, so that the concentration of EVAL becomes between about 5 mass % and about 12 mass %, for example, about 10 mass %.

As a next step, PEG DA nanoparticles containing everolimus can be prepared as described above. The nanoparticles having a size range between about 0.5 and 2.0 μm are suspended in the EVAL/DMSO/DMF solution described above. The suspension can contain between about 15 mass % and 25 mass %, for example, about 20 mass % of the nanoparticles. The suspension can be constantly stirred to prevent flocculation of the nanoparticles. The EVAL-primed stent can then be dipped into the suspension and centrifuged at 6,000 rpm for about 1 minute to yield a smooth, defect-free coating, defined as "stent coating I."

Example 2

Stent coating II containing nanoparticles can be formed. Stent coating II is the same as stent coating I described in Example 1, except instead PEG DA nanoparticles, above-described CAP-based nanoparticles incorporating everolimus can be used.

Following the fabrication of stent coating II, a topcoat composition to control the drug release rate can be prepared, comprising between about 0.1 mass % and about 15 mass %, for example, about 2.0 mass % EVAL and the balance a solvent system, for example, a solvent system including a 50:50 (mass) blend of DMAC and ethanol. In a manner identical to the application of the primer layer, the topcoat composition can be applied over stent coating II. A number of spray passes can be performed followed by final baking at about 50° C. for about 2 hours to form the topcoat layer.

Example 3

A stent can be coated with a primer layer as described in Example 1. Next, PEG DA nanoparticles containing actinomycin D (AcD) can be prepared as described above. The nanoparticles having a size range between about 0.5 and 2.0 μm can be suspended in methanol. The suspension can contain between about 40 mass % and 60 mass %, for example, about 50 mass % of the nanoparticles. The suspension can be constantly stirred to prevent flocculation of the nanoparticles. The EVAL-primed stent can then be dipped into the suspension and centrifuged at 2,000 rpm for about 1 minute to yield a smooth, defect-free coating. A topcoat composition to control the drug release rate can be prepared and applied as described in Example 2 to form the topcoat layer.

Example 4

A stent can be coated with a primer layer as described in Example 1. Next, a suspension of PEG DA nanoparticles in methanol can be prepared as described in Example 3. The ends of EVAL-primed stent can then be dipped into the suspension. Approximately 20% of the length of the stent on either end can be dipped, followed by centrifugation at 1,000 rpm for about 30 seconds to yield a smooth, defect-free coating which covers only the ends of the stent and leaving the central portion of the stent uncovered. A topcoat composition to control the drug release rate can be prepared and applied as described in Example 2 to form the topcoat layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for incorporating an active agent on an implantable medical device, the method comprising:
   (a) fabricating nanoparticles containing the active agent;
   (b) dispersing the nanoparticles in an organic phase to make a suspension; and
   (c) applying the suspension onto the implantable medical device such that the nanoparticles are incorporated on the implantable medical device, and stirring the suspension during the application,
   wherein the implantable medical device is a stent; and
   wherein the application comprises dipping the implantable medical device into the suspension.

2. The method of claim 1, wherein the fabrication of the nanoparticles comprises:
   (a) preparing a water-in-oil emulsion comprising the active agent dispersed in an organic solvent polymer solution;
   (b) converting the water-in-oil emulsion to a water-in-oil-in-water emulsion; and
   (c) extracting the organic solvent from the water-in-oil-in-water emulsion to form the nanoparticles.

3. The method of claim 2, wherein the polymer is selected from the group consisting of poly(L-glycolic acid), poly(D-lactic acid), poly(L-lactic acid), poly(L-lactide), poly(D,L-lactide), poly(glycolide), poly(butylene terephtalate-co-ethylene glycol), poly(ethylene-co-vinyl alcohol), poly(vinyl acetate), poly(butyl methacrylate), poly(methyl methacrylate), polyurethanes, poly(caprolactone), polyanhydrides, polydiaxanone, polyorthoesters, polyamino acids, poly(trimethylene carbonate), and mixtures and combinations thereof.

4. The method of claim 2, wherein the organic solvent is selected from the group consisting of methylene chloride, cyclooctane, cyclohexane, cycloheptane, para-xylene, dimethylformamide, dimethylsulfoxide, chloroform, dimethylacetamide and mixtures thereof.

5. The method of claim 1, wherein the fabrication of the nanoparticles comprises:
   (a) preparing a water-in-oil emulsion comprising a polymer, an organic solvent and the active agent; and
   (b) extracting the organic solvent from the water-in-oil-emulsion to form the nanoparticles.

6. The method of claim 1, wherein the fabrication of the nanoparticles comprises:
   (a) preparing a solution comprising the active agent and a polymer in an organic solvent; and
   (b) spraying the solution to form the nanoparticles.

7. The method of claim 1, wherein the fabrication of the nanoparticles comprises:
   (a) preparing a solution comprising the active agent and a polymer in an organic solvent;
   (b) atomizing the solution by spraying;
   (c) freezing the atomized solution; and
   (d) extracting the organic solvent to form the nanoparticles.

8. The method of claim 1, wherein the fabrication of the nanoparticles comprises:
   (a) preparing a water-in-oil emulsion comprising a cross-linkable compound and the active agent; and
   (b) cross-linking the cross-linkable compound to form the nanoparticles.

9. The method of claim 1, wherein the organic phase comprises an organic solvent or a solution of a polymer.

10. A coating for an implantable medical device, the coating fabricated by the method of claim 1.

11. The method of claim 1, wherein the nanoparticles comprise a polymer.

12. The method of claim 9, wherein the mass ratio of nanoparticles to polymer in the suspension is between about 1:2 and 1:10.

13. The method of claim 12, wherein the polymer in the polymer solution is poly(ethylene-co-vinyl alcohol) and the active agent is everolimus.

14. The method of claim 1, further comprising centrifuging the implantable medical device subsequent to the application of the suspension.

15. The method of claim 9, wherein the organic phase comprises a solution of a polymer.

* * * * *